(12) United States Patent
Loipetsberger (10) Patent No.: US 8,648,903 B2
(45) Date of Patent: Feb. 11, 2014

(54) DEVICE FOR EVALUATING IMAGES OF WELD SPOTS ON A CARRIER MATERIAL

(75) Inventor: Mario Loipetsberger, Oberndorf (AT)

(73) Assignee: Fronius International GmbH, Pettenbach (AT)

( * ) Notice: Subject to any disclaimer, the term of this patent is extended or adjusted under 35 U.S.C. 154(b) by 1147 days.

(21) Appl. No.: 12/227,534

(22) PCT Filed: Apr. 24, 2007

(86) PCT No.: PCT/AT2007/000190
§ 371 (c)(1),
(2), (4) Date: Nov. 20, 2008

(87) PCT Pub. No.: WO2007/140492
PCT Pub. Date: Dec. 13, 2007

(65) Prior Publication Data
US 2009/0128625 A1   May 21, 2009

(30) Foreign Application Priority Data
Jun. 2, 2006   (AT) .................................. A 962/2006

(51) Int. Cl.
  H04N 7/18   (2006.01)
  B23K 9/10   (2006.01)
  B23K 9/12   (2006.01)
(52) U.S. Cl.
  USPC .................. 348/90; 219/109; 219/124.34
(58) Field of Classification Search
  USPC .......................................................... 348/90
  See application file for complete search history.

(56) References Cited

U.S. PATENT DOCUMENTS

| 4,168,430 A | * | 9/1979 | Denis et al. ............... 250/338.1 |
| 4,236,781 A | * | 12/1980 | Arimura ........................ 348/79 |
| 4,578,561 A | * | 3/1986 | Corby et al. ............ 219/124.34 |
| 4,863,268 A | * | 9/1989 | Clarke et al. ............... 356/237.2 |
| 5,051,872 A | | 9/1991 | Anderson |
| 5,684,530 A | * | 11/1997 | White ......................... 348/131 |
| 6,414,261 B1 | | 7/2002 | Maetschke |

(Continued)

FOREIGN PATENT DOCUMENTS

| JP | 2-167450 | 6/1990 |
| JP | 2005-537933 | 12/2005 |

(Continued)

OTHER PUBLICATIONS

Russian Office Action with English translation of relevant parts.
International Search Report.
A.J. Ishlinskij "Politechnitscheskij slowar", Sowjetskaya enziklopedija, M., 1980. (Russian OA).

*Primary Examiner* — Firmin Backer
*Assistant Examiner* — James Edwards
(74) *Attorney, Agent, or Firm* — Collard & Roe, P.C.

(57) ABSTRACT

The invention relates to a device (22) for evaluating an image (20) produced on a carrier material (8) by spot welding of a weld spot (19) using an optical image-detecting unit (23), comprising a camera (24) which consists of at least one detection means (25) and one lens (26). In order to create an evaluation device (22), by means of which the optical quality testing of spot-weld joints can be improved, the image-detecting means (23) comprises an illumination device (27) with a diffusor (28) for diffusively and homogeneously illuminating an image (20) of the spot-welding on the carrier material (8). Furthermore, the invention relates to a welding tool (1) for a spot-welding plant, in particular a welding gun (2), having an evaluation device (22) for analyzing an image (20) of a spot weld (19) on a carrier material (8).

21 Claims, 4 Drawing Sheets

(56) References Cited

U.S. PATENT DOCUMENTS

| | | | |
|---|---|---|---|
| 7,259,349 B2 | 8/2007 | Stieglbauer et al. | |
| 2004/0114035 A1* | 6/2004 | White | 348/131 |
| 2005/0179805 A1* | 8/2005 | Avron et al. | 348/340 |
| 2006/0163213 A1* | 7/2006 | Stieglbauer et al. | 219/109 |

FOREIGN PATENT DOCUMENTS

| | | |
|---|---|---|
| RU | 2 141 075 | 11/1999 |
| RU | 2 157 948 | 10/2000 |
| RU | 2 235 802 | 9/2004 |
| WO | WO 2004/022278 | 3/2004 |

* cited by examiner

DEVICE FOR EVALUATING IMAGES OF WELD SPOTS ON A CARRIER MATERIAL

CROSS REFERENCE TO RELATED APPLICATIONS

This application is the National Stage of PCT/AT2007/000190 filed on Apr. 24, 2007, which claims priority under 35 U.S.C. §119 of Austrian Application No. A 962/2006 filed on Jun. 2, 2006. The international application under PCT article 21(2) was not published in English.

The invention relates to a device for evaluating an image produced on a carrier material by spot welding of a weld spot using an optical image-detecting unit, comprising a camera which consists of at least one detection means and one lens, for a system for monitoring the quality of spot weldings.

Furthermore, the invention relates to a welding tool for a spot-welding plant, in particular a welding gun, comprising at least one retention arm for an electrode for resistance welding, and to a positioning unit for a carrier material, in particular a tape, which can be guided past the electrode, provided for producing an image of a weld spot, in particular of a nugget, with an evaluation device being arranged for analyzing the image.

A method for quality monitoring of a spot welding is known from U.S. Pat. No. 6,414,261 B1, wherein a weld spot is analyzed by evaluating image data recorded by a video camera. Here, the upper side of the workpiece, on which some welding has been done, is recorded by a video camera, whereupon the image information will be calculated for assessing quality of the spot welding. Here, it is disadvantageous that no homogeneous light conditions prevail on the workpiece in the region of the weld joint, since the upper side of the workpiece is exposed to the outside and, thus, the illumination is at least partly determined by the ambient light. Furthermore, the information content of the recorded image material is affected and/or falsified by the reflections on the shiny and/or reflecting surface of the metal and/or by the shadows cast by the evaluation device or by the components of the welding plant, thus complicating an exact and differentiated quality evaluation of the weld joint.

This method and similar prior-art methods known for monitoring the quality of spot weldings involve the substantial drawback of a video camera not fixed to the spot-welding gun. This means that the video camera has to be positioned on the respective surface of the spot welding by means of an appropriate positioning unit. Accordingly, the workpiece may also be positioned, e.g. below the video camera. Consequently, it takes considerable efforts to analyze the weld spot with such systems, the correspondingly involved time efforts included.

Furthermore, a method for monitoring the quality of spot weldings is known from WO 2004/022278 A1, wherein a tape or foil is inserted between the electrodes and the metal sheets to be welded, with the tape or foil being designed such that a mirror-inverted, in particular proportional, image or imprint of the weld spot formed on the workpiece will be created by the welding process on the tape or foil. Thereafter, the mirror-inverted image or imprint on the tape or foil will be detected and evaluated by the evaluation means, wherein the image or imprint allows for the evaluation means or control and/or evaluation means of a welding device to draw conclusions as to the size, shape and position of the weld spot. Here, it is again disadvantageous that the optical detection of the image or imprint is effected by means of conventional cameras and/or lenses, whereby the quality of the images taken may be strongly affected by variable or inhomogeneous ambient illumination and reflections in the imprint.

Consequently, the prior-art methods and devices for monitoring the quality of spot weldings involve the drawback that it is not possible to evaluate the welding results in an automated manner immediately after the welding process and at defined and constant light conditions and/or ambient conditions and irrespective of the workpiece.

Thus, it is the object of the present invention to provide an evaluation device and/or welding tool, by means of which optical quality testing of spot-weld joints may be improved. The invention also includes the object of improving efficiency of the production sequence of a spot-welding plant by quality testing, in particular by an automated quality testing in the direct environment of the welding place.

The inventive object is discretely achieved in that the image-detecting unit comprises an illumination device with a diffusor for diffusively and homogeneously illuminating the image of the spot welding on the carrier material. This results in the advantage of the image being evenly illuminated on the carrier material so that it is rendered feasible to obtain an unfalsified and as natural an image record as possible by means of a camera in order to subsequently allow for some electronic image processing to be performed for assessing the quality of the weld joint. The even and diffusive illumination of the image prevents bright and/or dark areas, in particular shadows, and/or reflections in the region of the image and/or recording range of the camera. The diffusor allows for such homogeneous illumination of the image so that substantially constant light conditions will be created and that it will be possible to assess different images on the carrier material under the same analysis criteria. Thus, a more objective and differentiated assessment of the quality of weld joints is rendered possible.

If the illumination device is adjusted to indirectly illuminate the carrier material in the direction of the camera, it is feasible to generate diffusive light in a simple fashion, which allows for a homogeneous illumination of the carrier material.

A diffusive illumination of the carrier material with high luminous intensity is rendered possible if the illumination device comprises a light source arranged for large-area illumination of a carrier material, with the diffusor having a reflector which, at the reflection surface, reflects the light beams generated by the light source in the direction of the carrier material. Since the light source does not directly radiate the reflecting carrier material, reflections and/or bright regions on the surface of the carrier material may be prevented.

By means of a reflector comprised of a light-impermeable and/or opaque material which has a low degree of absorption for visible radiation, a particularly efficient illumination of the carrier material is allowed for since the output of the radiation impinging on the reflector and the reflected radiation are almost identical so that a great portion of the radiation energy generated may be used for illuminating the carrier material.

A particularly cost-effective and functional design may be achieved if the material of the reflector is selected from the group of plastics.

If the reflection surface is bright-colored and/or has brightly reflecting properties, an illumination on the carrier material is rendered possible which is as natural as possible and, in terms of color, as unfalsified as possible.

A design is particularly advantageous in which the reflection surface is white, in particular matt white, since the whole spectrum of visible light, i.e. white light, will be reflected at the white surface, allowing for a natural coloring on the surface of the carrier material and high luminous intensity, at the same time.

Due to its suitable reflection properties a silver-colored, in particular a matt-silver-colored, reflection surface has proven to be also advantageous.

Likewise, it is advantageous if the reflection surface has at least partially a curvature and encloses an interior in a dome-like manner. Thus, it is rendered possible to illuminate a carrier material present below the reflection surface from several sides and/or to illuminate its entire circumference, allowing for a very homogeneous and reflection-free illumination of the carrier material.

It is also advantageous if the reflection surface with the curvature, delimits a recess in a housing which forms a dome. Thus, the housing of the illumination device may at the same time serve as a reflector and a reflecting surface, with the dome completely shielding the housing from light radiation from outwards. Thereby, it is rendered possible to illuminate an image on the carrier material by using only the illumination device, allowing for a controllable illumination and reproducibility of the measurement results. Here, it has proven to be particularly advantageous if the dome, on a lower side opposing the reflection surface, has an opening, in the region of which the carrier material may be guided past.

By the measure that the dome has substantially the form of a half shell, with the reflection surface present on the wall of the dome running in a preferably half-spherical manner, the opposite arrangement of the illumination means in the side region of the dome allows for creation of a particularly compact structure of an indirect illumination device.

Here, the dome has an opening, preferably on a lower side opposing the reflection surface, in the region of which the carrier material may be guided past.

Due to its simple and cost-effective structure an embodiment variant, in which the reflector is formed by the material of the housing, is advantageous.

Illumination properties which are independent of the nature of the housing, with said properties optionally being variable and/or adjustable maybe achieved by an embodiment variant in which the reflector is provided on an inner side of the housing as a coat or lacquer coat. Thus, the reflector may be specifically adapted to a carrier material in order to achieve an optimum illumination result.

Thus, the light source is arranged to oppose the reflection surface in the region of the curvature, a very even indirect illumination of the carrier material is rendered possible.

By an embodiment, in which the light source is comprised of at least one light-emitting diode, preferably an LED ring consisting of several light-emitting diodes, the long service life of light diodes offers the advantage that maintenance of the illumination device will only rarely be required, and the illumination device provides the advantage that heat development and power consumption will be low.

Furthermore, a compact structure of the illumination device is allowed for, wherein particularly an LED ring comprising at least three circularly arranged light-emitting diodes located in a side region of the dome provides for a design which is compact and, in terms of illumination, efficient.

An embodiment variant, in which the image-detecting unit has a pinhole lens including a hole, is of advantage. Thus, it is rendered possible that only a very small region is non-reflective, with said region corresponding to the cross-section of the pinhole and being, e.g., located within the dome, wherein the pinhole lens may be designed as a part of the diffusor. Since the hole in the lens, i.e. the pinhole, is of relatively small cross-section, disturbing darkenings on the image of the carrier material are prevented, said darkenings resulting from the reflection of the camera through the hole. Thereby, the quality of the image recorded by the camera may be significantly improved since the darkening on the picture produced by the reflection of the camera is negligibly small compared to the darkening with usual lens objectives.

By the measure that the lens has a reflector surrounding the hole, the reflection of the camera on the image of the carrier material is prevented in a particularly effective manner.

A design is advantageous in which the lens of the camera is arranged on an upper side of the dome opposing the carrier material since the image will be detected by the camera in an undistorted and proportional way, thus facilitating the evaluation of the image information recorded.

Furthermore, an embodiment variant is advantageous in which a transparent protective element, e.g. made of plastics or glass, is provided in front of the image-detecting unit so as to protect the same from contaminations. Thereby, contaminations are prevented from entering the interior of the dome and from affecting the illumination properties in the interior. Moreover, it is thereby not required to clean the interior of the illumination device.

The inventive object is furthermore discretely achieved by a welding tool which comprises an evaluation device designed at least partially according to the above description and, in particular, according to any one of claims 1 to 21. Such a welding tool is advantageous since it allows for the image of a spot-weld joint to be recorded and/or analyzed by the evaluation device directly after the welding process has been finished.

A design is also of advantage in which the evaluation device is arranged on an inner side of the retention arm, with the carrier material, which includes the image, being guided past the inner side after the welding process has been finished since the carrier material may be transported away along the surface of the welded joint and, at the same time, the evaluation device may process the image on the carrier material in the vicinity of the welded joint. Thus, a separate working station for analyzing the image on the carrier material can be omitted, simplifying the production sequence of a weld joint and reducing the production costs.

A design is also advantageous in which the retention arm is formed in an L-type manner as known per se and has a bending, and in which the evaluation device is arranged in a region of the bending. Thereby, the evaluation device is arranged in the direct vicinity of the electrode and/or welded joint, wherein the welding tool will not be restricted in its movement since the evaluation device is arranged in the region of the bending and, consequently, the range of use of the welding tool will not be restricted by the evaluation device and an evaluation of the weld spot will be possible directly after the latter has been produced. By the measure that after a welding process has been finished, the positioning unit for arranging the carrier material will be located on the inner side of the retention arm below the evaluation device, in particular below the opening of the dome, there is the possibility to advantageously automate the analysis and/or processing of the image on the carrier material, allowing for an economic and efficient assessment of the quality of a spot-welded joint.

The present invention will be explained in more detail by way of the enclosed schematic drawings.

Therein.

Figure 1:
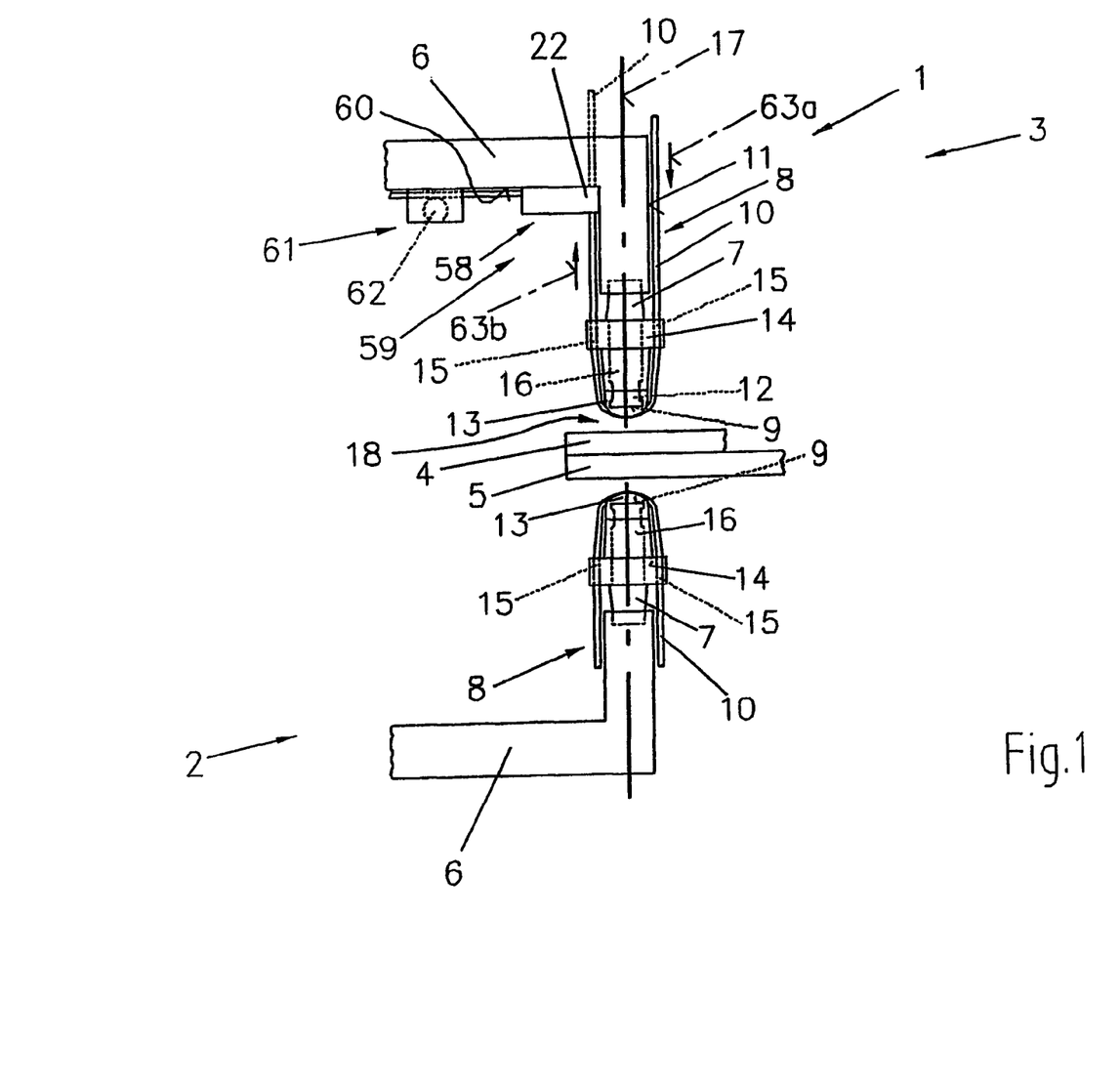
FIG. 1 shows a side view of a spot-welding plant with an inventive welding tool comprising an inventive evaluation device.

FIG. 1 shows a welding tool 1 in the form of a welding gun 2 of a spot welding plant 3 for resistance welding of at least two components such as, e.g. metal sheets 4, 5. Preferably, the welding tool 1 is used for robot applications for automated production of spot-weld joints. The welding tool 1 has, e.g., two bended or L-type retention arms 6 for receiving one electrode 7 each, with the electrode 7 being connected to a non-illustrated current source of the spot-welding plant 3. Furthermore, the welding tool 1 is designed for receiving and guiding a carrier material 8 which is guided past over a tip 9 of the electrode 7 via at least one retention arm 6. Preferably, the carrier material 8 is comprised of a foil or a tape 10 which is deformable and, in its longitudinal direction, displaceable along a surface 11 of the retention means 6. For displacing and/or conveying the carrier material 8, the welding tool 1 and/or the welding plant 3 comprise(s), e.g., a below-described positioning unit for conveying and/or winding and unwinding the tape 10 running past the electrode 7.

The tape 10 may be guided around the electrode 7 in the most various manners, which is why only an exemplary embodiment will be shortly explained in the following. Here, a dielectric spacing element 13 is arranged about the electrode 7 in the region of an electrode cap 12 and/or a contact surface of the electrode 7 with the metal sheet 4, 5. The spacing element 13 is, e.g., movably mounted on the electrode 7 such that additional pressure will be applied onto the metal sheets 4, 5 via the spacing element 13. Moreover, the moveable mounting of the spacing element 13 results in that after a welding process has been finished, the spacing element 13 will lift the tape 10 off the electrode 7, i.e. in that during or after opening of the welding gun 2 the spacing element 13 will self-dependently lift the tape 10 off the tip 9 and/or the electrode cap 12, whereas during closing of the welding gun 2 the spacing element 13 will be shifted relative to the electrode 7, whereby the tape 10 comes to abut on the electrode 7.

Furthermore, the welding tool 1 may comprise a support element 14 having guide channels 15 for receiving the carrier material 8. An adjustment means 16, in particular a spring element, is provided between the support element 14 and the spacing element 13, thus allowing for the latter to be displaced in the direction of the longitudinal center axis 17 of the electrode 7, with appropriate pressure being applied. To this end, the adjustment means 16 is designed to be deformable or spring-elastic.

Figure 2:
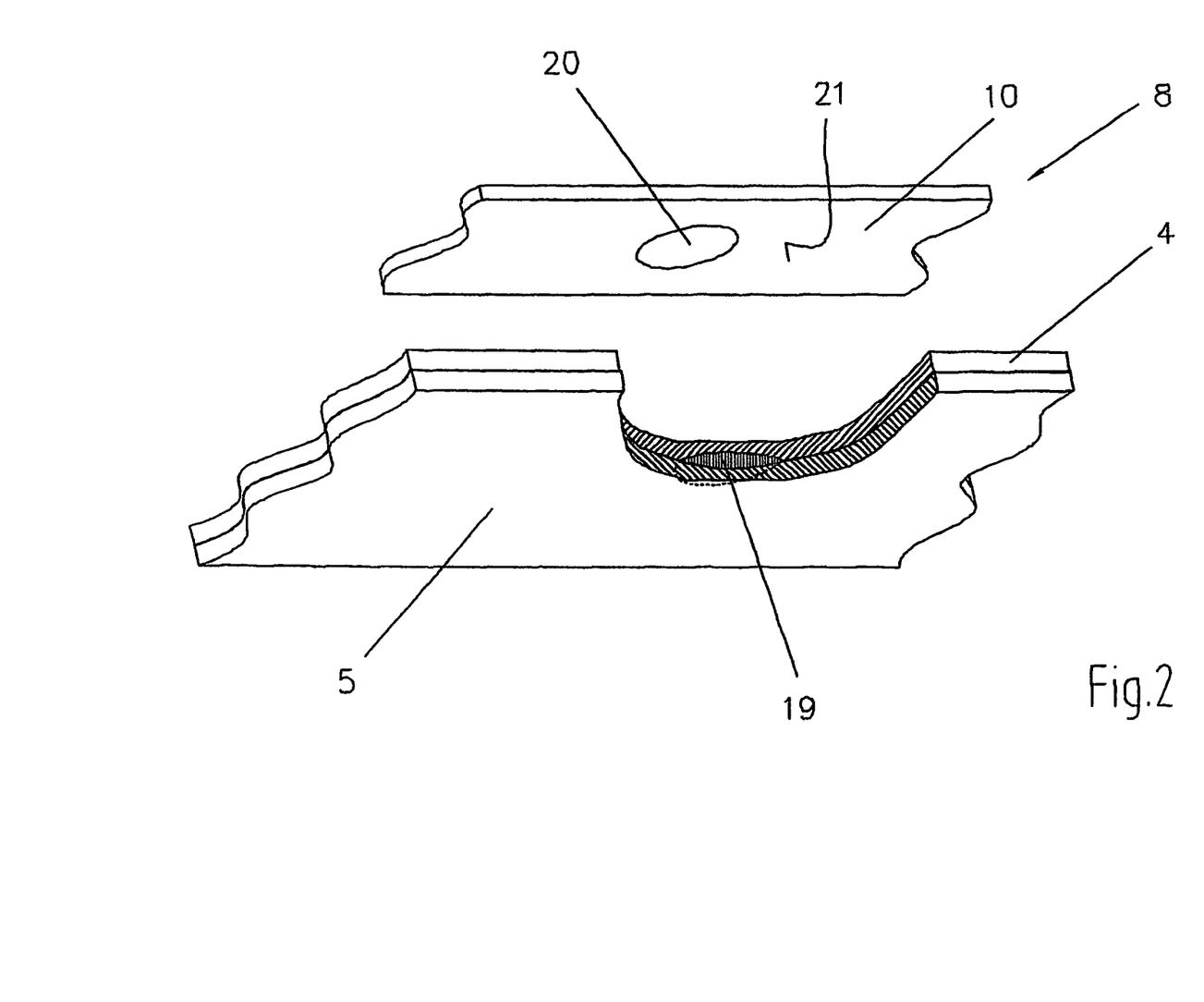
FIG. 2 shows a partially sectioned oblique view of welded metal sheets in the region of a weld spot.

By means of the welding tool 1, the metal sheets 4, 5 are mechanically pressed against each other via the electrodes 7 during the whole spot-welding process. During the spot-welding process the metal of two components to be connected is connected by melting-on and subsequent solidifying both, wherein, due to the high ohmic resistance between the components which prevails when a current starts to flow, a high output is converted into heat energy, leading to the metals being melted. After the melted mass has solidified at a weld joint 18, the metal sheets 4, 5 are connected via a weld spot 19 or a nugget, as is schematically illustrated in FIG. 2.

For assessing the quality of the weld spot 19, the carrier material 8 is provided with the carrier material 18 being arranged directly above the weld joint 18 during the welding process. The radiation and/or effect arising when the components are being welded, in particular the heat released by the geometric extension of the weld spot 19, causes a mirror-inverted image 20 of the weld spot 19 to be produced on the carrier material 8, with the image 20 being arranged in the region of the tip 9 of the electrode 7 on a side 21 facing the metal sheet 4, 5. After the welding has been done, a displacement of the tape 10 may be effected in its longitudinal direction via the positioning unit so as to allow for the evaluation device 22 to perform an analysis of the carrier material 8, irrespective of the position of the metal sheets 4, 5 and the site of processing. Such a method and the devices associated therewith have already been known from WO 2004/022278 A1 of the applicant, which is why reference is made thereto for further details on possible designs of the welding plant 3, the welding tool 1 and process sequences. At least some parts of the invention described in WO 2004/022278 A1 may be part of the present inventive subject matter.

Figure 3:
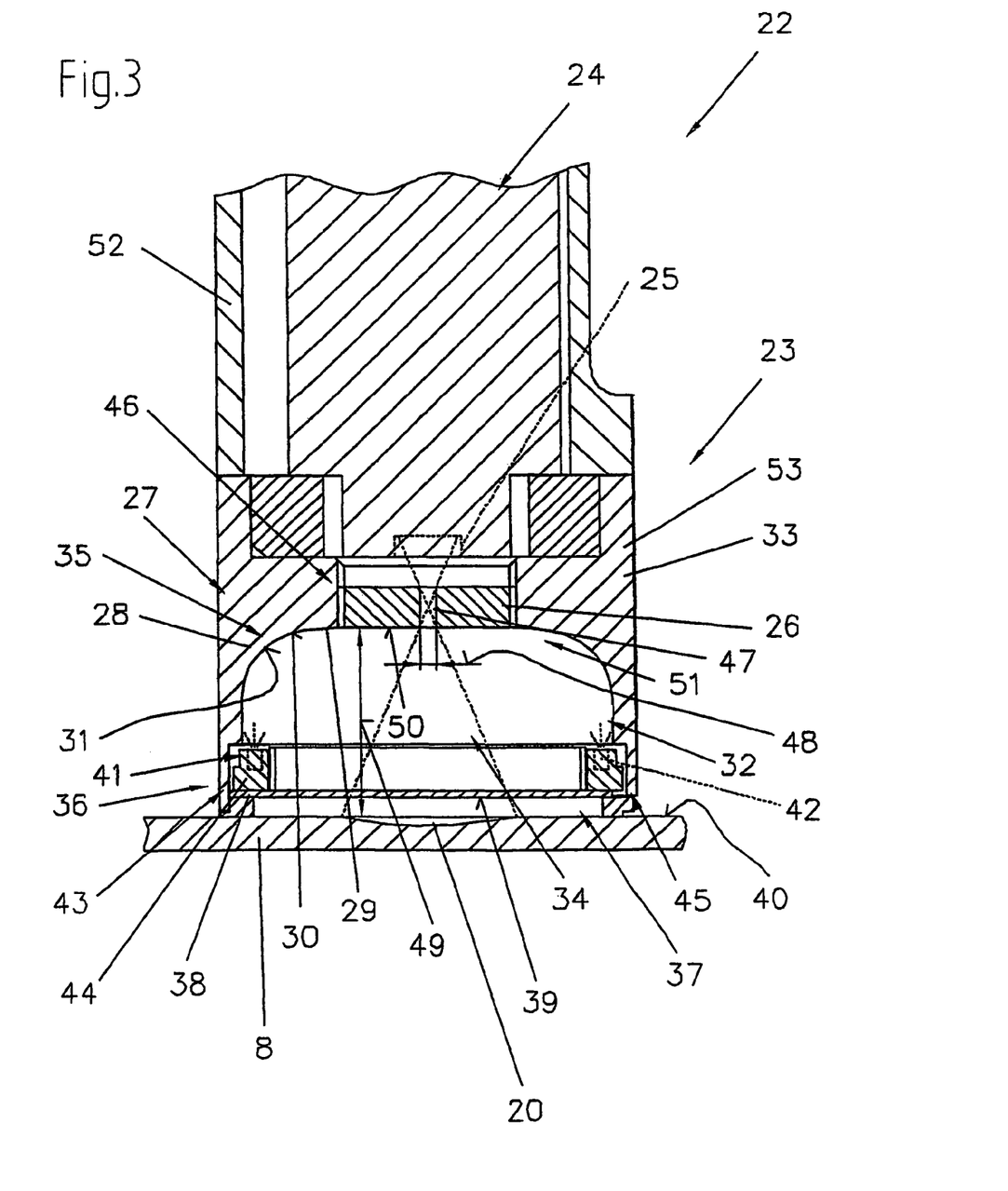
FIG. 3 shows a schematic sectional view of an embodiment variant of the inventive evaluation device.

FIG. 3 shows a possible embodiment variant of the inventive evaluation device 22. The evaluation device 22 is part of a system for monitoring the quality of spot weldings. This system is designed for property analysis of the weld spot 19, e.g. geometric variables, such as position, form and size of the weld spots 19. Image information of the image 20 recorded by the carrier material 8 is used for the analysis, wherein the optical detection of the image 20 is effected via the evaluation device 22. The evaluation device 22 has an image-detecting unit 23 with at least one camera 24. The camera 24 has a detection means 25 and a lens 26, wherein the detection means 25 is comprised of a sensor for converting light into image data, and the lens 26 is designed for adjusting the image properties of the image 20. Preferably, the detection means 25 is comprised of a semiconductor detector, e.g. a CCD camera chip (CCD—charge coupled device) or a CMOS camera chip (CMOS—complementary metal oxide semiconductor), which detects the image 20 of the weld spot 19 which will subsequently be digitized by an electronics. The detection means 25 and the lens 26 may form a common structural unit, with an electronics (not illustrated in detail) of the camera 24 being arranged at a different site in the evaluation device 22 and connectable to the detection means 25 via lines, networks, bus systems, etc. Thus, a more compact construction of the evaluation device 22 can be achieved. The system for monitoring quality assessment and/or the evaluation device 22 may comprise an evaluation logic which performs the property analysis of the image 20, with the evaluation logic being preferably comprised of a program logic provided in a memory. For example, the evaluation logic has been installed on a computer which receives the image information from the evaluation device 22 via a network (internet, intranet, etc.). Such evaluation logics have been known to those skilled in the art in the field of industrial image processing, which is why they will not be further discussed.

A controlled illumination of the carrier material 8 and/or the image 20 is necessary so as to allow the evaluation logics to perform an exact and diversified quality assessment of weld spots 19. This is achieved by the inventive image-detecting unit 23, which comprises an illumination device 27 designed for a diffusive and homogeneous illumination, and/or a so-called incident-light illumination, of the image 20 of a spot welding on a carrier material 8. The diffusive illumination causes a reflection-free and even coloring on the image 20 on the highly-reflective carrier materials 8 and/or tapes 10 so that there will be no falsification and/or loss of optical information on the image 20 by recordal with the camera 24. Thus, the properties of the weld spot 19 may be concluded from the image in a very fine graduation and reliable manner.

The illumination device 27 comprises a diffusor 28 for generating diffusive light, said diffusor 28 scattering the impinging light radiation in different directions. In the embodiment variant shown the illumination device 27 is designed for indirectly illuminating the carrier material 8, for the purpose of which the diffusor 28 has a reflector 29 reflecting the light beams impinging on a reflection surface 30 in the direction of the carrier material 8. Here, the reflector 29 is made of light-impermeable and/or opaque material, which has a low degree of absorption of electromagnetic radiation in the frequency range of light. For example, the material of the reflector 29 is selected from the group of plastics, wherein the plastics preferably is bright-colored. In particular, the material of the reflector 29 may be made of white or light-gray plastics so that bright and/or white light will be reflected by the reflector 29 in the direction of the carrier material 8. According to a further advantageous embodiment variant the reflector 29 is silver-colored. Furthermore, the reflection surface 30 of the reflector 29 may be dulled or roughened so as to provide for an increased scattering of impinging light beams.

The illumination device 27 may also be designed for directly illuminating the carrier material 8. Here, the diffusor 28 may be comprised of a semi-transparent plate and/or layer, e.g. made of plastics, opacified glass or the like, or of a transparent plate having a roughened surface, with the latter being radiated with light on an upper side so that diffusive light at the bottom side will be radiated in the direction of the carrier material 8.

The illumination of the carrier material 8 is preferably effected by a large-area light source or a large-area reflector 29 so as to allow for an illumination of the carrier material 8 which is as homogeneous as possible.

Figure 4:
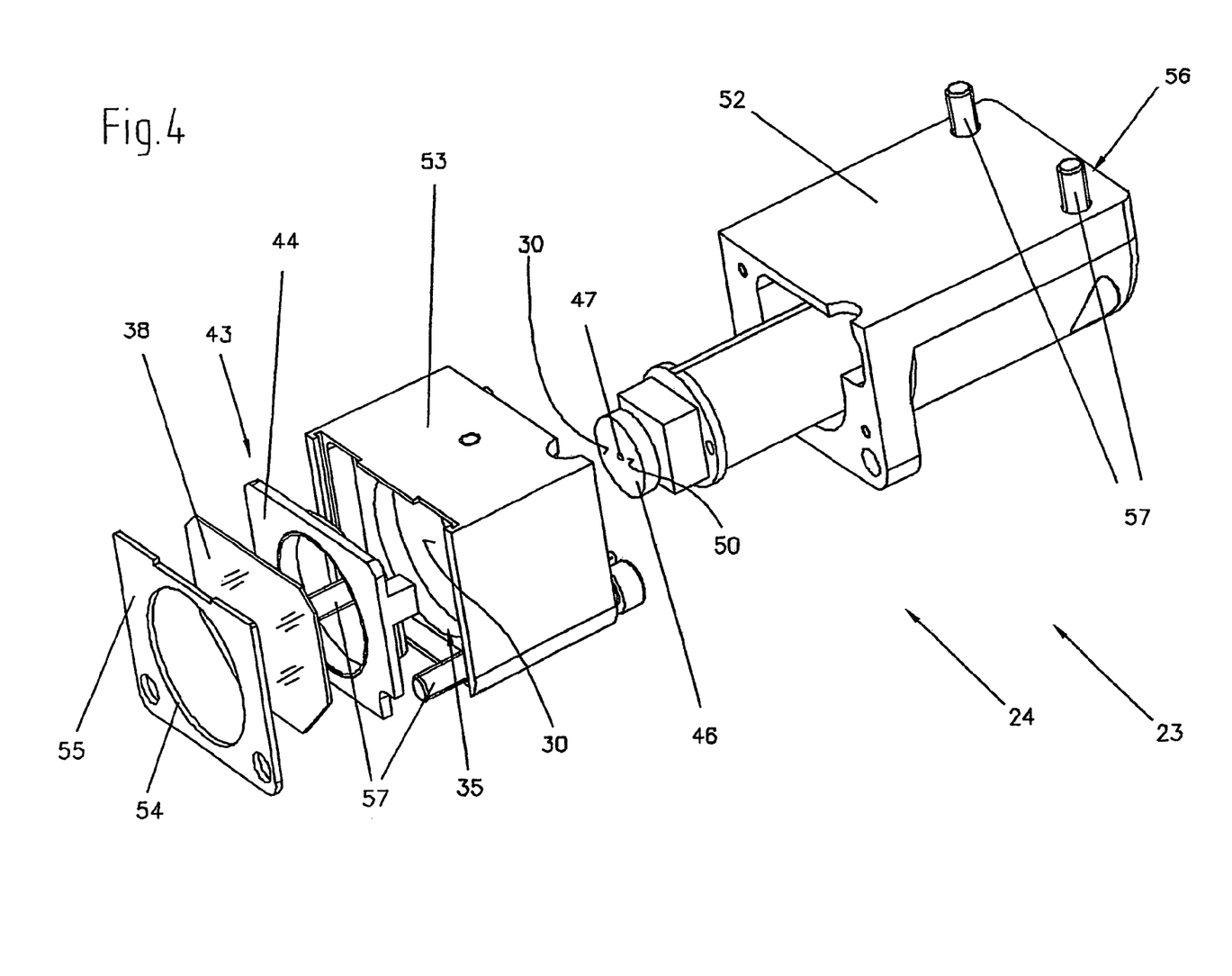
FIG. 4 shows an exploded view of an embodiment variant of the inventive evaluation device.

According to the exemplary embodiment illustrated in FIGS. 3 and 4 the reflection surface 30 comprises a curvature 31 enclosing an interior 32 in a dome-like manner. The illumination device 27 comprises a housing 33 with a recess 34 which forms a dome 35 which encloses the interior 32 with the reflection surface 30. In its front-side end region 36, the dome 35 has an opening 37 which may be closed by a protective element 38 which particularly is plate-shaped and light-permeable and/or transparent. The carrier material 8 positioned at a bottom side 39 of the protective element 38 facing away from the dome 35 is illuminated via the illumination device 27, which illuminates the interior 32 of the dome 35, so that a surface 40 of the carrier material 8 will be visible from the interior 32 and the image 20 will be able to be detected by the camera 24.

Furthermore, a cleaning device may be provided which is comprised, e.g., of a wiper, a compressed air jet or the like, and the carrier material 8 will be cleaned from contaminations in the region of the image 20. Thus, contaminations of the protective element 38 may be prevented, whereby the light-permeability of the protective element 38 will not be negatively affected.

The illumination device 27 comprises a light source 41 which is preferably formed by at least one LED (light-emitting diode) 42. Preferably, several light-emitting diodes 42 form one LED ring 44. The LED ring 44 may, e.g., consist of two light-emitting diodes 42 opposing each other diametrically. Preferably, the LED ring 44 has at least three, in particular more than five, light-emitting diodes 42 which are arranged along a periphery of the LED ring 44 in an equally-distanced manner. Preferably, the light-emitting diodes 42 of the LED ring 44 are designed to emit white light. Likewise, the light-emitting diodes 42 may emit multi-colored, in particular red, green or blue light. Of course, the LED ring 44 may, e.g., also be comprised of an LED array 43.

The LED ring 44 is arranged in the end region 36 and/or in the region of the opening 37 of the dome 35 and extends along a lateral region 45 of the housing 33 in a circular or an annular manner. Here, the light-emitting diodes 42 are arranged such that they will emit light in the direction of the reflection surface 30, i.e. light will be radiated by the light-emitting diodes 42 in the direction oriented away from the carrier material 8 and/or the opening 37. Appropriate measures allow for a lateral radiation, whereby a reflection onto the tape 10 will be prevented and, at the same time, a better radiation of the light cone will be achieved. The umbrella-type curvature 31 of the reflection surface 30 causes a diffusive reflection of the light and a homogeneous illumination of the interior 32 and/or the carrier material 8 arranged below the interior 32. Preferably, the dome 35 is designed to have the form of a half-shell, and, in particular, substantially the form of a semi-sphere.

In the inventive exemplary embodiment it is further provided that the lens 26 of the camera 24 is comprised of a pinhole lens 46. The pinhole lens 46 comprises a hole 47 of a small diameter 48 so that determination of the image size of the imaged subject or the image 20 is allowed for with a simple and compact structure. Preferably, the diameter 48 is only a fraction of a millimeter or few millimeters, in particular of from 0.1 mm to 5 mm, so that only the image 20 will be imaged on the detection means 25. To this end, the pinhole lens 46 is arranged to oppose the carrier material 8 and to be spaced from the same by a distance 49. Here, the distance 49 determines the factor of proportionality, with which the image 20 will be imaged on the detection means 25. Furthermore, the pinhole lens 46 has a bottom side 50 with diffusively-reflecting properties. To this end, a reflector 29 including the reflection surface 30 extends on the bottom side 50 of the pinhole lens 46, said reflector 29 preferably being of the above-described design. Thus, the bottom side 50 forms a region of the reflection surface 30, whereby the light generated by the light source 41 will not be reflected in the region of the hole 47 of a comparably small cross-section only. This non-reflective region is, however, of such a small size that there will be no visible or negligibly small reflection of the camera 24 on the carrier material 8 and a homogeneous illumination of the image 20 on the carrier material 8 will be given.

In the exemplary embodiment, the pinhole lens 46 is arranged preferably on an upper side 51 and/or a vertex of the dome 35 so as to allow for the image 20 of the carrier material 8 arranged below the interior 32 to be detected via the detection means 25. Such a vertical arrangement of the pinhole lens 46 above the image 20 on the carrier material 8 enables an undistorted recordal of the image 20 in a proportional size, allowing for an efficient processing of the image information recorded.

As is shown in FIG. 4, the housing 33 may consist of several parts, in particular a main housing 52 and a dome housing 53. The protective element 38 and/or the LED ring 44 may be fixed to the dome housing 53 via a fastening frame 53, which has an aperture 54, via fastening elements 56, in particular screws 57.

A further discrete solution of the inventive object resides in a welding tool 1 for the spot-welding plant 3, in particular the welding gun 2. The welding tool 1 comprises retention arms 6 for electrodes 7 for resistance welding and comprises the positioning unit for guiding and/or feeding a carrier material 8 or a tape 10, which has been guided past the electrode 7, wherein a spot-welding process allows for an image 20 of a nugget to be generated on the carrier material 8, said image 20 being analyzable by the evaluation device 22. According to the discrete solution, the evaluation device 22 is at least partly designed according to the above description. It should be noted that in the exemplary embodiment described below, the carrier material 8 is comprised of the tape 10.

Preferably, the evaluation device 22 is arranged directly on one of the retention arms 6, wherein the tape 10 provided with the image 20 is guided past the evaluation device 22 or guided through the same for evaluation purposes. According to FIG. 1, the retention arm 6 has a bending 58 formed by a curvature or buckling, with the retention arm 6 being in particular L-shaped. The evaluation device 22 is arranged in a region 59 of the bending 58 provided on the inner side 60 of the retention arm 6. After a welding process, the carrier material 8 comprising the image 20 will be guided past along the inner side 60 so as to allow for an evaluation of the welding result to be performed immediately after the welding process. Of course, the evaluation device 22 may be adapted to all geometries of the retention arms 6 so as to enable for the inventive evaluation device 22 to carry out the optical quality testing of spot-weld joints. It is also possible, e.g., to integrate the evaluation device 22 in one or both retention arm(s) 6 and to correspondingly guide the tape 10 past the evaluation device 22. Here, it is advantageous that the evaluation device 22 does in no way restrict accessibility and/or movement of the spot-welding plant 3.

For this purpose, the welding tool 1 or the spot-welding plant 3 has a positioning unit 61 for the carrier material 8. According to the exemplary embodiment shown, the positioning unit 61 is designed for displacing the tape 10 guided around the electrode 7, wherein the displacement is, e.g., effected in a pulsewise manner by a defined feed after every finished welding process. To this end, the positioning unit 61 has a drive member 62, which is in particular controllable by a control unit of the spot-welding plant 3. When the tape 10 is being displaced, it moves in the direction indicated by the arrows 63a and 63b so that the tape 10 will be guided past the evaluation device 22. The tape 10 may, e.g., be arranged below the opening 37 of the dome 35 so as to allow for the camera 24 to record the image 20. Here, via the guiding channel 15 and/or further guiding means, the tape 10 is guided past closely along the surface 11 of the retention arm 6. After the tape 10 has been guided past the evaluation device 22, it may be fed as desired, e.g., along the surface 11 of the retention arm 6, or transversely through the retention arm 6 via a guiding means, as is illustrated in FIG. 1 by dotted lines.

Preferably, the image is recorded by guiding the tape 10 past the evaluation device 20 via the positioning unit 61, with the camera 24 automatically recording the image 20. This means that the tape 10 is just drawn past the camera 24 and, at the same time, the surface of the tape 10, and thus of the weld spot 19, is continuously recorded. This renders unnecessary an exact positioning of the weld spot 19 in front of the camera 24 since the evaluation logic analyzes the optimum image of the weld spot 19 based on the image information received.

Thus, the carrier material 8 may be analyzed immediately after the welding process has been carried out, wherein this analysis may be performed in a completely automated manner. Here, there is no need for the carrier material 8 to be supplied to a working station separately designed in addition to the welding tool 1 but the carrier material 8 may be fed to its next destination immediately after the welding process and the analysis have been performed.

Furthermore, instead of being fixed to at least one of the retention arms 6, the evaluation device 22 may be arranged on an external apparatus/working station. In order to allow for an evaluation of the weld spot 19, the tape 10 will be removed from the welding gun 2 after it has been completely consumed and will be inserted into the apparatus/working station, whereupon the individual images will be evaluated. The order of the spot weldings allows for an allocation of the weld spots 19 so that erroneous weld spots 19 may be identified and edited at any time.

In general, it should be noted that each of the retention arms 6 may have a separate evaluation device 22 such that, e.g., different carrier materials 8, which may be adapted to different materials of the metal sheets 4, 5, may be processed separately for each retention arm 6 by the respective evaluation device 22. However, in the exemplary embodiment shown, the welding tool 1 has only one evaluation device 22, which evaluates the tape 10 allocated to the metal sheet 4.

The individual embodiments shown in FIGS. 1 to 4 may be the subject matter of the discrete solutions according to the invention. The respective objects and solutions according to the invention are to be learned from the detailed descriptions of these figures.

The invention claimed is:

1. A welding tool for a spot-welding plant, including at least one retention arm for an electrode provided for resistance welding, and including a positioning unit for a tape guided past and protecting the electrode, said tape being provided for producing an image of a weld spot and increasing welding quality, with an evaluation device being arranged for analyzing the image,
    wherein the evaluation device comprises an optical image-detecting unit comprising:
        a camera comprising:
            at least one detection element; and
            one lens; and
        an illumination device with a diffusor for diffusively and homogeneously illuminating the image on the tape, the illumination device being configured for indirect illumination of the tape in the direction of the camera and having a light source arranged for large-area illumination of the tape, the diffusor comprising a reflector having a reflector surface, the reflector, at the reflection surface, reflecting the light beams generated by the light source in the direction of the tape.

2. The welding tool according to claim 1, wherein the reflector comprises a light-impermeable and/or opaque material which has a low degree of absorption for visible radiation.

3. The welding tool according to claim 2, wherein the material of the reflector comprises a plastic material.

4. The welding tool according to claim 1, wherein the reflection surface of the reflector is bright-colored and/or has brightly reflecting properties.

5. The welding tool according to claim 1, wherein the reflection surface of the reflector is white.

6. The welding tool according to claim 1, wherein the reflection surface of the reflector is silver-colored.

7. The welding tool according to claim 1, wherein the reflection surface has at least partially a curvature and encloses an interior in a dome-like manner.

8. The welding tool according to claim 7, wherein the reflection surface with the curvature delimits a recess in a housing which forms a dome.

9. The welding tool according to claim 8, wherein the dome substantially has the form of a half-shell, and
    wherein the reflection surface present on the wall of the dome extends in a half-spherical manner.

10. The welding tool according to claim 8, wherein the dome, on a lower side opposing the reflection surface, has an opening, in the region of which the tape may be guided past.

11. The welding tool according to claim 8, wherein the reflector comprises the material of the housing.

12. The welding tool according to claim 8, wherein the reflector is applied onto an inner side of the housing to serve as a coating or lacquer coat.

13. The welding tool according to claim 8, wherein the one lens of the camera is arranged on an upper side of the dome opposing the tape.

14. The welding tool according to claim 1, wherein the light source is arranged to oppose the reflection surface in the region of the curvature.

15. The welding tool according to claim 1, wherein the light source comprises at least one light-emitting diode.

16. The welding tool according to claim 15, wherein the at least one light-emitting diode comprises an LED ring comprising at least three circularly arranged light-emitting diodes, which are located in a side region of the dome.

17. The welding tool according to claim 1, wherein the optical image-detecting unit has a pinhole lens including a hole.

18. The welding tool according to claim 17, wherein the hole of the pinhole lens is surrounded by the reflector with the reflection surface.

19. The welding tool according to claim 1, wherein a transparent protective element is provided in front of the optical image-detecting unit so as to protect the optical image-detecting unit from contaminations.

20. The welding tool according to claim 1, wherein the evaluation device is arranged on an inner side of the at least one retention arm, with the tape, which is provided with the image, being guided past this inner side after a welding process has been finished.

21. The welding tool according to claim 1, wherein the at least one retention arm is formed in an L-type manner and has a bending, and wherein the evaluation device is arranged in a region of the bending.

* * * * *